(12) United States Patent
Datta et al.

(10) Patent No.: US 10,966,681 B2
(45) Date of Patent: Apr. 6, 2021

(54) SYSTEMS AND METHODS FOR DETECTING PULMONARY ABNORMALITIES USING LUNG SOUNDS

(71) Applicant: Tata Consultancy Services Limited, Mumbai (IN)

(72) Inventors: Shreyasi Datta, Kolkata (IN); Anirban Dutta Choudhury, Kolkata (IN); Parijat Deshpande, Pune (IN); Sakyajit Bhattacharya, Kolkata (IN); Arpan Pal, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 335 days.

(21) Appl. No.: 15/912,234

(22) Filed: Mar. 5, 2018

(65) Prior Publication Data

US 2019/0008475 A1    Jan. 10, 2019

(30) Foreign Application Priority Data

Jul. 4, 2017 (IN) .............................. 201721023532

(51) Int. Cl.
*A61B 7/00* (2006.01)
*A61B 5/00* (2006.01)
(Continued)

(52) U.S. Cl.
CPC ............ *A61B 7/003* (2013.01); *A61B 5/7267* (2013.01); *A61B 7/04* (2013.01); *A61B 5/0816* (2013.01)

(58) Field of Classification Search
None
See application file for complete search history.

(56) References Cited

U.S. PATENT DOCUMENTS

| 8,758,262 B2 | 6/2014 | Rhee et al. |
| 9,545,219 B2 | 1/2017 | Moussavi et al. |
| (Continued) | | |

FOREIGN PATENT DOCUMENTS

| CA | 2267378 | 4/1998 |
| WO | WO 2016/002004 A1 | 1/2016 |

OTHER PUBLICATIONS

Kulkarni, P. G., and A. D. Sahasrabudhe. "Investigations on mother wavelet selection for health assessment of lathe bearings." The International Journal of Advanced Manufacturing Technology 90.9-12 (2017): 3317-3331. (Year: 2016).*

(Continued)

*Primary Examiner* — Jacqueline Cheng
*Assistant Examiner* — Jairo H Portillo
(74) *Attorney, Agent, or Firm* — Finnegan, Henderson, Farabow, Garrett & Dunner, LLP (57) ABSTRACT

Identification of pulmonary diseases involves accurate auscultation as well as elaborate and expensive pulmonary function tests. Also, there is a dependency on a reference signal from a flowmeter or need for labelled respiratory phases. The present disclosure provides extraction of frequency and time-frequency domain lung sound features such as spectral and spectrogram features respectively that enable classification of healthy and abnormal lung sounds without the dependencies of prior art. Furthermore extraction of wavelet and cepstral features improves accuracy of classification. The lung sound signals are pre-processed prior to feature extraction to eliminate heart sounds and reduce computational requirements while ensuring that information providing adequate discrimination between healthy and abnormal lung sounds is not lost.

15 Claims, 10 Drawing Sheets

(51) Int. Cl.
*A61B 7/04* (2006.01)
*A61B 5/08* (2006.01)

(56) References Cited

U.S. PATENT DOCUMENTS

| | | | | |
|---|---|---|---|---|
| 2003/0055348 | A1* | 3/2003 | Chazal | A61B 5/04325 600/509 |
| 2009/0156950 | A1 | 6/2009 | Savic | |
| 2012/0184825 | A1* | 7/2012 | Ben David | A61B 7/003 600/301 |
| 2014/0126732 | A1* | 5/2014 | West | H04R 1/46 381/67 |
| 2014/0155773 | A1* | 6/2014 | Stamatopoulos | A61B 7/003 600/529 |
| 2014/0171815 | A1* | 6/2014 | Yang | A61B 5/4818 600/529 |
| 2014/0276229 | A1 | 9/2014 | Ikeda | |
| 2015/0057512 | A1* | 2/2015 | Kapoor | A61B 5/0205 600/324 |
| 2017/0119303 | A1* | 5/2017 | Yadollahi | A61B 5/11 |

OTHER PUBLICATIONS

Kaushik, Geeta, H. P. Sinha, and Lillie Dewan. "Biomedical Signals Analysis by DWT Signal Denoising With Neural Networks." Journal of Theoretical & Applied Information Technology 62.1 (2014). (Year: 2014).*

Göğüş, Fatma Z., Bekir Karlik, and Güneş Harman. "Classification of asthmatic breath sounds by using wavelet transforms and neural networks." International Journal of Signal Processing Systems 3.2 (2015): 106-111. (Year: 2015).*

Shardlow, Matthew. "An analysis of feature selection techniques." The University of Manchester 1 (2016): 1-7. (Year: 2016).*

* cited by examiner

SYSTEMS AND METHODS FOR DETECTING PULMONARY ABNORMALITIES USING LUNG SOUNDS

PRIORITY CLAIM

This U.S. patent application claims priority under 35 U.S.C. § 119 to: Indian Patent Application No. 201721023532, filed on 4 Jul. 2017. The entire contents of the aforementioned application are incorporated herein by reference.

TECHNICAL FIELD

The embodiments herein generally relate to detection and analyses of auscultation sound signals, and more particularly to systems and methods for detecting pulmonary abnormalities using lung sounds.

BACKGROUND

There has been a massive increase in the occurrence of pulmonary diseases worldwide, due to increasing pollution, effect of burning biomass, human habits like smoking and the like. Obstructive Airway Diseases (OAD) like Asthma or Chronic Obstructive Pulmonary Disease (COPD), characterized by narrowing of the airways has emerged as reasons for major concern. Identification of abnormal lung sounds is a first step in diagnoses of such diseases. Auscultation to screen the presence of abnormality is an entirely manual process and lung sounds being inherently aperiodic signals, an abnormality may not surface throughout a recording for a subject, making diagnosis difficult. Further, skewed doctor-to-patient ratio in developing countries often leads to failure in timely diagnosis. Traditional known methods for identification of abnormal lung sounds use a reference flowmeter signal along with lung sounds to label the respiratory phases or manually separate them out. Some conventional methods involve deep learning to identify features for lung sound analysis. However, such features are often not physically interpretable and hence not relevant to the medical fraternity for screening pulmonary abnormalities.

SUMMARY

Embodiments of the present disclosure present technological improvements as solutions to one or more of the above-mentioned technical problems recognized by the inventors in conventional systems.

In an aspect, there is provided a processor implemented method comprising: receiving a plurality of auscultation sound signals to be classified from a plurality of subjects; pre-processing the received plurality of auscultation sound signals, wherein the pre-processing comprises resampling of the plurality of auscultation sound signals and removing heart sound signals to obtain a plurality of lung sound signals; extracting one or more of spectral features, spectrogram features, wavelet features and cepstral features from the plurality of lung sound signals; selecting a plurality of discriminative features from the extracted features; and classifying the plurality of lung sound signals based on the selected discriminative features.

In another aspect, there is provided a system comprising: one or more data storage devices operatively coupled to the one or more processors and configured to store instructions configured for execution by the one or more processors to: receive a plurality of auscultation sound signals to be classified from a plurality of subjects; pre-process the received plurality of auscultation sound signals by resampling the plurality of auscultation sound signals and removing heart sound signals to obtain a plurality of lung sound signals; extract one or more of spectral features, spectrogram features, wavelet features and cepstral features from the plurality of lung sound signals; select a plurality of discriminative features from the extracted features; and classify the plurality of lung sound signals based on the selected discriminative features.

In yet another aspect, there is provided a computer program product comprising a non-transitory computer readable medium having a computer readable program embodied therein, wherein the computer readable program, when executed on a computing device, causes the computing device to: receive a plurality of auscultation sound signals to be classified from a plurality of subjects; pre-process the received plurality of auscultation sound signals by resampling the plurality of auscultation sound signals and removing heart sound signals to obtain a plurality of lung sound signals; extract one or more of spectral features, spectrogram features, wavelet features and cepstral features from the plurality of lung sound signals; select a plurality of discriminative features from the extracted features; and classify the plurality of lung sound signals based on the selected discriminative features.

In an embodiment of the present disclosure, the resampling comprises down-sampling the plurality of auscultation sound signals to a pre-defined frequency is based on a range of frequencies that provide optimum discrimination between healthy and abnormal lung sounds.

In an embodiment of the present disclosure, the step of removing heart sound signals is based on Empirical Mode Decomposition method.

In an embodiment of the present disclosure, the step of extracting features comprises dividing the plurality of lung sound signals into a plurality of overlapping windows.

In an embodiment of the present disclosure, the step of extracting spectral features comprises: computing periodograms for each of the plurality of overlapping windows; and averaging the periodograms to obtain a Power Spectral Density (PSD) estimate curve for the plurality of lung sound signals.

In an embodiment of the present disclosure, the extracted spectral features are areas under a normalized Power Spectral Density (PSD) estimate curve corresponding to a pre-defined number of frequency bands from 0-1.5 kHz ($PS_1$ to $PS_{15}$), ratio of the spectral power below 500 Hz ($P_1$) to that from 500 Hz to 1500 Hz ($P_2$), spectral centroid ($S_{cent}$), spectral flux ($S_{flux}$), spectral rolloff ($S_{roll}$) and spectral kurtosis ($S_{kurt}$), wherein the pre-defined number of frequency bands is selected such that optimum discrimination between healthy and abnormal lung sounds is achieved.

In an embodiment of the present disclosure, the extracted spectrogram features are median spectral powers ($SP_1$ to $SP_{58}$) across the plurality of overlapping windows, wherein the median spectral powers are computed for a pre-defined number of equally spaced frequencies between 0.15 kHz-1.5 kHz of the plurality of lung sound signals, the pre-defined number of equally spaced frequencies being based on the computational complexity and frequency resolution.

In an embodiment of the present disclosure, the step of extracting wavelet features comprises: selecting a best mother wavelet in each window of the plurality of overlapping windows based on maximum energy and minimum Shannon entropy criteria; decomposing the plurality of lung sound signals using the best mother wavelet into decomposition levels; and computing median of absolute values of approximation and detail coefficients for the decomposition levels.

In an embodiment of the present disclosure, the extracted wavelet features ($W_1$ to $W_{21}$) are (i) the median of absolute values of approximation and detail coefficients for the decomposition levels and (ii) ratios thereof across sub-bands of the plurality of overlapping windows.

In an embodiment of the present disclosure, the extracted cepstral features are mean ($mfccm_i$ and $lfccm_i$) and standard deviation ($mfccsd_i$ and $lfccsd_i$) of Mel Frequency Cepstral Coefficients (MFCC) and Linear Frequency Cepstral Coefficients (LFCC).

In an embodiment of the present disclosure, the step of selecting a plurality of discriminative features from the extracted features comprises: ranking the extracted features in decreasing order of importance; and selecting a plurality of discriminative features based on the optimal no. of features that result in a high performance value and a low standard deviation of a set of pre-defined performance metrics, wherein the set of predefined performance metrics comprise accuracy, sensitivity, specificity and area under the receiver operating characteristic curve.

It is to be understood that both the foregoing general description and the following detailed description are exemplary and explanatory only and are not restrictive of the embodiments of the present disclosure, as claimed.

BRIEF DESCRIPTION OF THE DRAWINGS

The embodiments herein will be better understood from the following detailed description with reference to the drawings, in which.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Before setting forth the detailed explanation, it is noted that all of the discussion below, regardless of the particular implementation being described, is exemplary in nature, rather than limiting.

The present invention deals with lung sound analysis for predicting pulmonary abnormalities. In case of pulmonary defects, abnormal lung sounds such as wheezes, crackles, squeaks, stridors, etc. are present when breathing. Systems and methods of the present disclosure facilitate classifying whether a lung sound is abnormal or healthy (normal) based on certain characteristic features, particularly spectral and spectrogram features. No manual labeling of respiratory cycles or segmentation of lung sounds into respiratory cycles is necessary.

Referring now to the drawings, and more particularly to FIGS. 1 through 7, where similar reference characters denote corresponding features consistently throughout the figures, there are shown preferred embodiments and these embodiments are described in the context of the following exemplary system and method.

Figure 1:
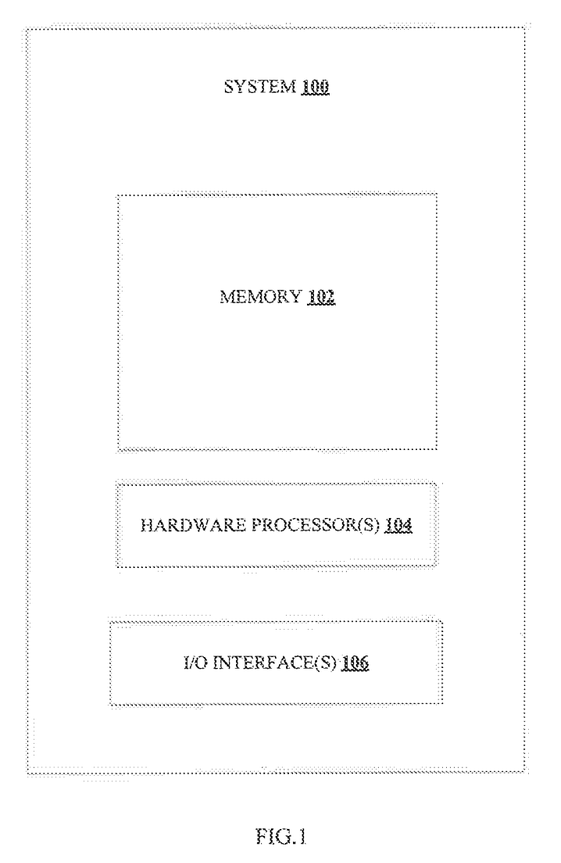
FIG. 1 illustrates an exemplary block diagram of a system for detecting pulmonary abnormalities using lung sounds, in accordance with an embodiment of the present disclosure.

FIG. 1 illustrates an exemplary block diagram of a system 100 for detecting pulmonary abnormalities using lung sounds, in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2:
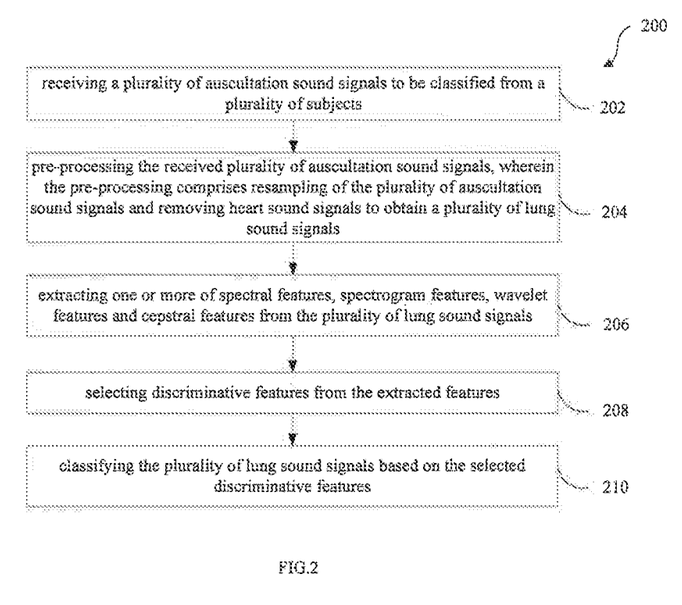
FIG. 2 is an exemplary flow diagram illustrating a computer implemented method for detecting pulmonary abnormalities using lung sounds, in accordance with an embodiment of the present disclosure.

FIG. 2 is an exemplary flow diagram illustrating a computer implemented method 200 for detecting pulmonary abnormalities using lung sounds, in accordance with an embodiment of the present disclosure. In an embodiment, the system 100 comprises one or more data storage devices or memory 102 operatively coupled to the one or more processors 104 and is configured to store instructions configured for execution of steps of the method 200 by the one or more processors 104.

The steps of the method 200 will now be explained in detail with reference to the components of the system 100 of FIG. 1. In accordance with the present disclosure, the one or more processors 104 are configured to receive, at step 202, a plurality of auscultation sound signals to be classified from a plurality of subjects. In an embodiment, acquisition of auscultation sound signals involves using a digital stethoscope. Lung sounds are inherently contaminated with heart sounds. Also, different sampling rates exist when different sources (types of stethoscopes) are used. In an embodiment, the one or more processors 104 are configured to pre-process the received plurality of auscultation sound signals at step 204. The step of pre-processing comprises resampling of the plurality of auscultation sound signals and removing undesired heart sound signals to obtain a plurality of lung sound signals. Heart sound signals may be removed by Empirical Mode Decomposition method. The resampling comprises down-sampling the plurality of auscultation sound signals to a pre-defined frequency based on a range of frequencies that provide optimum discrimination between healthy (normal) and abnormal lung sounds. In an embodiment, the auscultation sound signals are downsampled to 4 kHz (Nyquist theorem) as necessary information to classify lung sound signals into healthy and abnormal classes lies within 2 kHz.

In an embodiment, the one or more processors 104 are configured to extract, at step 206, one or more of spectral features, spectrogram features, wavelet features and cepstral features from the plurality of lung sound signals. In accordance with the present disclosure, adding two or more feature types enhances accuracy of classification of the lung sound signals as explained herein after. The step of extracting features firstly comprises dividing the plurality of lung sound signals (session) into a plurality of overlapping windows or segments.

Figure 3:
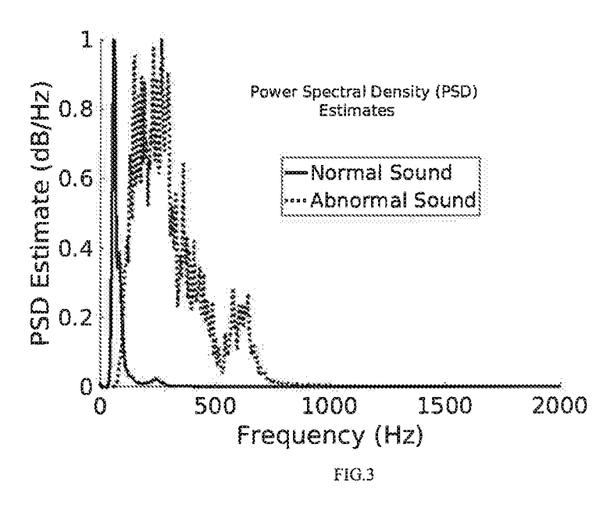
FIG. 3 illustrates Power Spectral Density (PSD) estimate curves for healthy and abnormal data pertaining to lung sound signals, in accordance with an embodiment of the present disclosure.

In accordance with the present disclosure, spectral characteristics of lung sound signals may be used to discriminate healthy and abnormal classes. Firstly, periodograms are computed for each of the plurality of overlapping windows. In an embodiment, Welch method may be used for computing the periodograms. The periodograms are then averaged to obtain a Power Spectral Density (PSD) estimate curve for the plurality of lung sound signals. FIG. 3 illustrates Power Spectral Density (PSD) estimate curves for healthy (normal) and abnormal data pertaining to lung sound signals, in accordance with an embodiment of the present disclosure. It may be noted that area under a normalized PSD curve is significantly higher for an abnormal sound compared to a healthy sound. However, the exact spread of the area varies with the degree and nature of the abnormality. In an embodiment, a normalized Welch PSD curve is obtained using windows of 1024 samples and 50% overlap at 15 frequency bands with overlapping windows of 1 sec. Accordingly, in accordance with the present disclosure, the spectral features that may be extracted to aid classification of the lung sound signals are areas under a normalized Power Spectral Density (PSD) estimate curve corresponding to a pre-defined number of frequency bands from 0-1.5 kHz ($PS_1$ to $PS_{15}$), ratio of the spectral power below 500 Hz ($P_1$) to that from 500 Hz to 1500 Hz ($P_2$), spectral centroid ($S_{cent}$), spectral flux ($S_{flux}$), spectral rolloff ($S_{roll}$) and spectral kurtosis ($S_{kurt}$), wherein the pre-defined number of frequency bands is selected such that optimum discrimination between normal and abnormal lung sounds is achieved.

Lung sound being nonstationary in nature, a spectrogram analysis reveals the change of frequency with time. For each session spectrograms with windows of length 512 and 480 point overlap were created using 512 point FFT. It is known that spectral power for lung sounds in the range of 0.15 kHz-1.5 kHz is significantly higher in abnormal lung sounds compared to healthy lung sounds. However, the exact spread of the frequency is strongly correlated with the nature of the abnormality. From the spectrogram, 58 equally spaced frequencies between 0.15 kHz-1.5 kHz are selected ensuring a trade-off between computational complexity and higher frequency resolution, after checking the performance during validation. For each such frequency, the median spectral power across all time windows are used, thereby getting spectral powers $SP_1$ to $SP_{58}$. The spectral power at each frequency is normalized with respect to the total spectral power at all frequencies. Thus, in accordance with the present disclosure, spectrogram features that may be extracted to aid classification of the lung sound signals are median spectral powers ($SP_1$ to $SP_{58}$) across the plurality of overlapping windows, wherein the median spectral powers are computed for a pre-defined number of equally spaced frequencies between 0.15 kHz-1.5 kHz of the plurality of lung sound signals, the pre-defined number of equally spaced frequencies being based on the computational complexity and frequency resolution.

Figure 4:
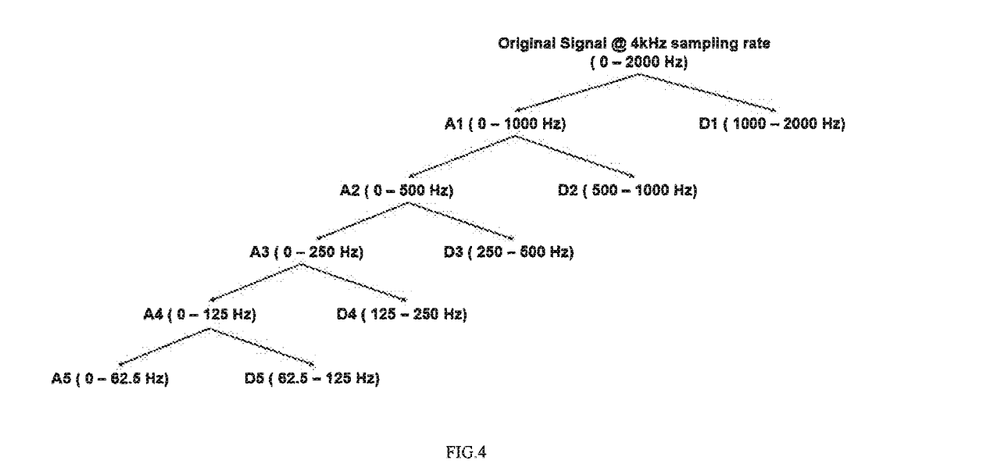
FIG. 4 illustrates wavelet decomposition showing regions of interest, in accordance with an embodiment of the present disclosure.

Discrete Wavelet Transform (DWT) represents a signal in multiple frequency bands by decomposing it into approximation and detail information. The decomposition level is determined by the frequency band of interest, wherein decomposing of the plurality of lung sound signals is done using a best mother wavelet selected in each window based on maximum energy and minimum Shannon entropy criteria For a signal sampled at 4 kHz (i.e. maximum information content till 2 kHz), the approximation ($A_i$) and detail ($D_i$) coefficients at the $i^{th}$ level, for all decomposition levels is illustrated in FIG. 4. Based on the region of interest on the frequency domain (0-2000 Hz), a median of the absolute values of the D1, D2, D3, D4, D5 and A5 coefficients as illustrated in FIG. 4 and their ratios over all windows are used as wavelet features ($W_1$ to $W_{21}$). In accordance with the present disclosure, the values of the coefficients are normalized with respect to all sub-bands of all the windows and the ratios of the features between all sub-bands are taken.

In accordance with the present disclosure, the cepstral features that may be extracted to aid classification of the lung sound signals are mean ($mfccm_i$ and $lfccm_i$) and standard deviation ($mfccsd_i$ and $lfccsd_i$) of Mel Frequency Cepstral Coefficients (MFCC) and Linear Frequency Cepstral Coefficients (LFCC). To extract these features, in an embodiment, the signals are divided into windows of 50 ms and 50% overlap and the signals are analyzed between 0-2000 Hz.

Table I herein below depicts all features and their respective indices used as reference in the present disclosure.

TABLE I

Description of features used

| Feature Index | Description |
|---|---|
| 1 to 20 | Spectral features: $PS_1$ to $PS_{15}$, $P_1/P_2$, $S_{cent}$, $S_{flux}$, $S_{roll}$, $S_{kurt}$ |
| 21 to 78 | Spectrogram features: $SP_1$ to $SP_{58}$ |
| 79 to 99 | Wavelet features: $W_1$ to $W_{21}$ |
| 100 to 179 | Cepstral Features: $mfccm_1$ to $mfccm_{20}$, $mfccsd_1$ to $mfccsd_{20}$, $lfccm_1$ to $lfccm_{20}$, $lfccsd_1$ to $lfccsd_{20}$ |

In an embodiment, the one or more processors (104) are configured to select, at step 208, a plurality of discriminative features from the extracted features of step 206. The step of selecting discriminative features is critical to avoid irrelevant or redundant features. In an embodiment, the step of selecting a plurality of discriminative features from the extracted features comprises ranking the extracted features in decreasing order of importance; and selecting a plurality of discriminative features based on the optimal no. of features that result in a high performance value and a low standard deviation of a set of pre-defined performance metrics. In an embodiment, Maximal Information Coefficient (MIC) based feature selection algorithm may be used. In an embodiment, the set of pre-defined performance metrics comprise accuracy, sensitivity, specificity and area under the receiver operating characteristic curve.

In an embodiment, the one or more processors (104) are configured to classify, at step 210, the plurality of lung sound signals based on the selected discriminative features. A linear Support Vector Machine (SUM) classifier may be used to classify the lung sounds based on the selected discriminative features. The tolerance of termination criterion may be set to 0.001, though experimentations over a validation set revealed no major change in performance with slight variation in the tolerance.

Results and Observations
Dataset:

A lung sound dataset comprising 52 lung sound signals equally distributed among healthy and abnormal classes was created from different data sources. The abnormal lung sound signals were obtained from a) RALE Lung Sound Repository and b) Steven Lehrer Lung Sound Repository. Both these data sources have lung sounds labelled by physicians to be healthy or having some form of abnormality. The abnormalities include different forms of wheezes and crackles along with squawks, stridors, grunting, squeaks and pleural rub. These were collected from subjects of various age groups and from different chest locations. Some of the healthy sounds were collected from healthy individuals working in the lab using either an in-house digital stethoscope that records audio data at 8 kHz through an android application on a Nexus 5 smartphone or the 3M Littmann Electronic Stethoscope Model 32005 at 4 kHz. Some other normal sounds were acquired from the RALE Lung Sound Repository. The sampling rates of the RALE data and Steven Lehrer data are respectively 11.025 kHz and 44.1 kHz. The lab data were collected from either tracheal position or posterior chest walls.

Performance Metrics:

Standard classification metrics accuracy, sensitivity and specificity were used to evaluate the performance of the methods of the present disclosure along with area (AUC) under the Receiver Operating Characteristics (ROC) curve, that shows the variation of the true positive rate with the false positive rate.

Figure 5:
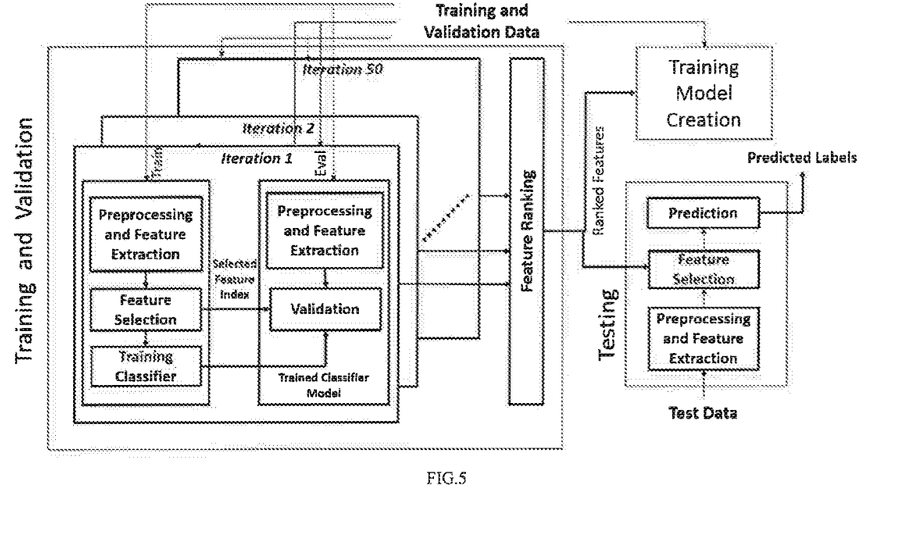
FIG. 5 illustrates a schematic representation of a supervised validation methodology, in accordance with an embodiment of the present disclosure.
Figure 6A:
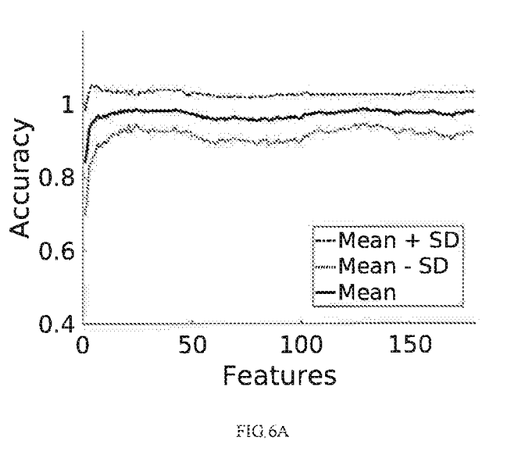
FIG. 6A through FIG. 6D illustrate graphical representations of performance metrics viz., accuracy, Area under Receiver Operating Characteristics curve, sensitivity and specificity respectively during validation phase with sequential addition of features in accordance with an embodiment of the present disclosure.
Figure 6B:
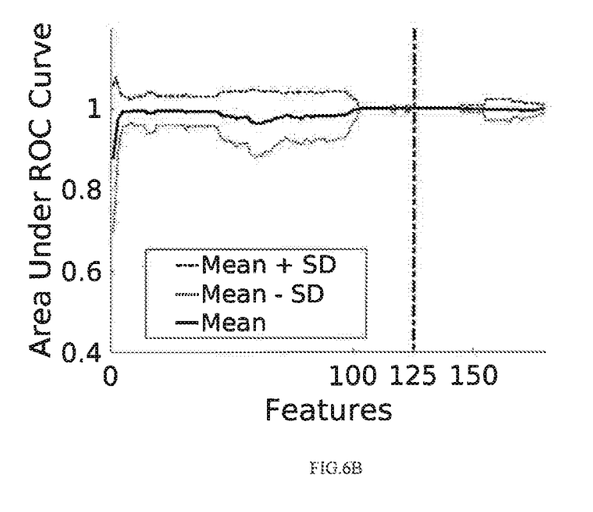
Figure 6C:
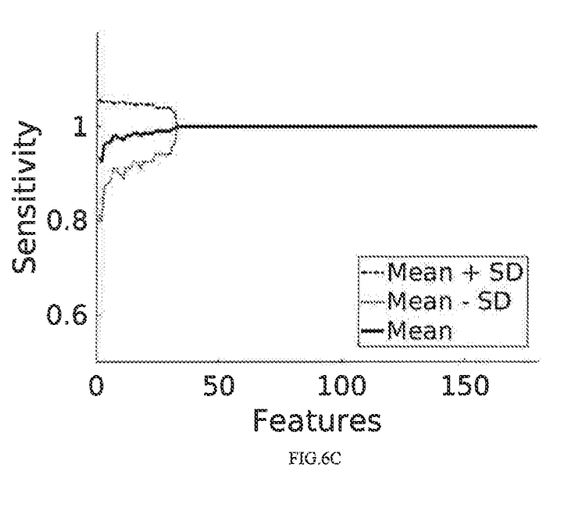
Figure 6D:
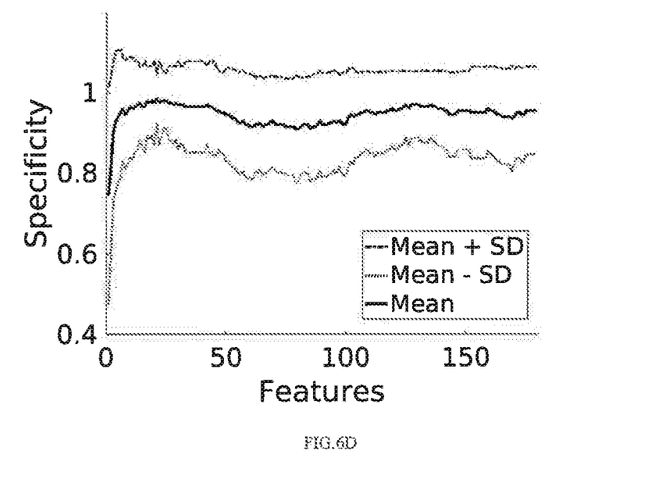

Results:

FIG. 5 illustrates a schematic representation of a supervised validation methodology, in accordance with an embodiment of the present disclosure. The dataset was separated into two subsets: a) for training and validation (validation phase—VP) and b) for testing (testing phase—TP). In VP, 70% of the data was randomly selected for training and the remaining 30% was used for evaluation. The training and evaluation subsets contain data with equally distributed samples from both healthy and abnormal classes. To mitigate the problem of relatively small sample size, the validation process was repeated for 50 times as shown in FIG. 5. For each such iteration, MIC was used to select the best features from the training subset only. Thereby the selected features and the training model were used to evaluate the performance of the evaluation set. For each iteration, features were sequentially added in order of decreasing importance and the performance was noted.

FIG. 6A through FIG. 6D illustrate graphical representations of performance metrics viz., accuracy, Area under Receiver Operating Characteristics curve, sensitivity and specificity respectively during validation phase with sequential addition of features in accordance with an embodiment of the present disclosure. The Mean±SD values of the performance metrics over all 50 iterations are shown in FIG. 6A through FIG. 6D with the sequential addition of features. A final rank list showing the best 16 features obtained from their median ranks over the 50 iterations is provided in Table II, along with the Mean±SD values for the respective features for each class.

TABLE II

Best 16 features selected after validation phase

| | | Rank | | | | | | | |
|---|---|---|---|---|---|---|---|---|---|
| | | 1 | 2 | 3 | 4 | 5 | 6 | 7 | 8 |
| | Index | 109 | 116 | 154 | 100 | 105 | 155 | 140 | 159 |
| Mean ± SD | Healthy | 6.5 ± 2.9 | −1.67 ± 0.78 | 1.55 ± 0.59 | 52.42 ± 15.89 | 4.72 ± 3.61 | 1.83 ± 0.85 | 49.36 ± 15.71 | 0.37 ± 0.25 |
| | Abnormal | −0.08 ± 3.47 | 0.14 ± 0.56 | −0.4 ± 1.2 | 25.89 ± 30.24 | −1.59 ± 5.44 | −0.08 ± 0.95 | 24.67 ± 29.62 | −0.02 ± 0.16 |

TABLE II-continued

Best 16 features selected after validation phase

| | | Rank | | | | | | |
|---|---|---|---|---|---|---|---|---|
| | | 9 | 10 | 11 | 12 | 13 | 14 | 15 | 16 |
| | Index | 19 | 143 | 54 | 63 | 64 | 12 | 62 | 65 |
| Mean ± SD | Healthy | 133.48 ± 52.65 | 5.78 ± 5.04 | $(37 \pm 15) \times 10^{-5}$ | $(22 \pm 9) \times 10^{-5}$ | $(21 \pm 9) \times 10^{-5}$ | $(19 \pm 13) \times 10^{-4}$ | $(23 \pm 9) \times 10^{-5}$ | $(20 \pm 9) \times 10^{-5}$ |
| | Abnormal | 248.52 ± 141.58 | −0.4 ± 3.41 | $(15 \pm 17) \times 10^{-4}$ | $(11 \pm 16) \times 10^{-4}$ | $(11 \pm 15) \times 10^{-4}$ | 0.65 ± 2.82 | $(12 \pm 20) \times 10^{-4}$ | $(9 \pm 13) \times 10^{-4}$ |

It may also be noted that the features proposed in accordance with the present disclosure provide clear evidence of discrimination between normal and abnormal lung sounds. In the final ordered feature list, 47 of the first 100 features are either the spectral or spectrogram features in accordance with the present disclosure which may be justified by the remarkable difference between the PSD estimates and spectrograms for the two classes of sound data (refer FIG. 3). To freeze the number of features, a high performance value with a low standard deviation of the metrics is chosen. As evident in FIG. 6B though performance value is high before the first 100 features, the standard deviation decreases and remains consistently low in the range of 100-150 features. As a tradeoff between the performance and computational requirements (which increases with the number of features) the first 125 features from VP are selected.

Figure 7A:
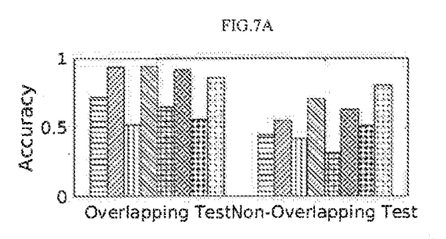
FIG. 7A through FIG. 7C illustrate graphical representations of performance metrics viz., accuracy, sensitivity and specificity respectively in accordance with an embodiment of the present disclosure when compared with methods known in the art.
Figure 7B:
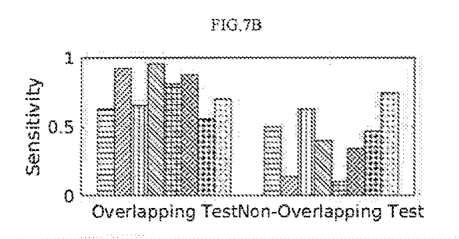
Figure 7C:
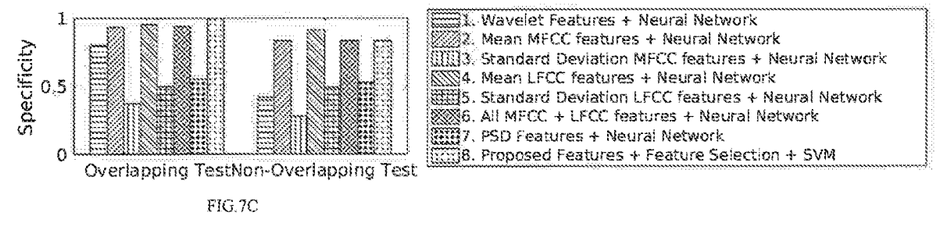

FIG. 7A through FIG. 7C illustrate graphical representations of performance metrics viz., accuracy, sensitivity and specificity respectively in accordance with an embodiment of the present disclosure when compared with methods known in the art. Results are reported for two test cases: (a) overlapping Test: VP and TP contain data from separate subjects but from overlapping data sources and (b) Non-overlapping Test: VP and TP contain data from separate subjects as well as non-overlapping data sources. The results in FIG. 7A through FIG. 7C show that though the prior arts produce decent performance for overlapping test, the performance drastically degrades for the non-overlapping Test. Particularly, the sensitivity, and hence accuracy, for methods 2, 4 and 6 of FIG. 7A through FIG. 7C (prior art), drops for the non-overlapping test. However, the method of the present disclosure maintains a consistently high performance (accuracy of 85% and 80% for overlapping and non-overlapping test respectively).

Thus in accordance with the present disclosure, systems and methods described herein above provide an automated lung sound analysis platform to identify abnormal lung sounds without the use of any reference signal from a flowmeter or labelling of the respiratory phases. Particularly spectral and spectrogram features have been identified which when used along with wavelet and cepstral features enhance accuracy of the classification of lung sound signals. An automated feature selection on a validation set followed by evaluation on a separate test data source ensures elimination of overfitting but still yields a high performance. Accuracy of classification remains high with a balance in the sensitivity and specificity.

The written description describes the subject matter herein to enable any person skilled in the art to make and use the embodiments of the present disclosure. The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments of the present disclosure may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules comprising the system of the present disclosure and described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The various modules described herein may be implemented as software and/or hardware modules and may be stored in any type of non-transitory computer readable medium or other storage device. Some non-limiting examples of non-transitory computer-readable media include CDs, DVDs, BLU-RAY, flash memory, and hard disk drives.

Further, although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope and spirit of disclosed embodiments being indicated by the following claims.

What is claimed is:

1. A processor implemented method (200) comprising:
   receiving a plurality of auscultation sound signals to be classified from a plurality of subjects (202);
   pre-processing the received plurality of auscultation sound signals, wherein the pre-processing comprises resampling of the plurality of auscultation sound signals and removing heart sound signals to obtain a plurality of lung sound signals (204);
   dividing the plurality of lung sound signals into a plurality of overlapping windows;
   extracting a set of features comprising two or more features types, wherein one of the features type is spectrogram features, and the other features type is selected from at least one of spectral features, wavelet features and cepstral features from the plurality of lung sound signals (206), wherein the extracted spectrogram features are median spectral powers (SP1 to SP58) across the plurality of overlapping windows, and wherein the median spectral powers are computed for a predefined number of equally spaced frequencies between 0.15 kHz-1.5 kHz of the plurality of lung sound signals, the pre-defined number of equally spaced frequencies being based on the computational complexity and frequency resolution;
   selecting a plurality of discriminative features from the extracted set of features (208), wherein the selection of the plurality of discriminative features comprises ranking the extracted set of features in a decreasing order of importance and selecting a plurality of discriminative features based on an optimal number of features that result in a high performance value and a low standard deviation of a set of pre-defined performance metrics; and
   classifying the plurality of lung sound signals based on the selected discriminative features (210).

2. The processor implemented method of claim 1, wherein the resampling comprises down-sampling the plurality of auscultation sound signals to a pre-defined frequency based on a range of frequencies that provide optimum discrimination between healthy and abnormal lung sounds.

3. The processor implemented method of claim 1, wherein the step of removing heart sound signals is based on Empirical Mode Decomposition method.

4. The processor implemented method of claim 1, wherein the step of extracting spectral features comprises:
   computing periodograms for each of the plurality of overlapping windows; and
   averaging the periodograms to obtain a Power Spectral Density (PSD) estimate curve for the plurality of lung sound signals.

5. The processor implemented method of claim 4, wherein the extracted spectral features are areas under a normalized Power Spectral Density (PSD) estimate curve corresponding to a pre-defined number of frequency bands from 0-1.5 kHz ($PS_1$ to $PS_{15}$), ratio of the spectral power below 500 Hz ($P_1$) to that from 500 Hz to 1500 Hz ($P_2$), spectral centroid ($S_{cent}$), spectral flux ($S_{flux}$), spectral rolloff ($S_{roll}$) and spectral kurtosis ($S_{kurt\_t}$), wherein the pre-defined number of frequency bands is selected such that optimum discrimination between healthy and abnormal lung sounds is achieved.

6. The processor implemented method of claim 1, wherein the step of extracting wavelet features comprises:
   selecting a best mother wavelet in each window of the plurality of overlapping windows based on maximum energy and minimum Shannon entropy criteria;
   decomposing the plurality of lung sound signals using the best mother wavelet into decomposition levels; and
   computing median of absolute values of approximation and detail coefficients for the decomposition levels.

7. The processor implemented method of claim 6, wherein the extracted wavelet features ($W_1$ to $W_{21}$) are (i) the median of absolute values of approximation and detail coefficients for the decomposition levels and (ii) ratios thereof across sub-bands of the plurality of overlapping windows.

8. The processor implemented method of claim 1, wherein the extracted cepstral features are mean ($mfccm_i$ and $lfccm_i$) and standard deviation ($mfccsd_i$ and $lfccsd_i$) of Mel Frequency Cepstral Coefficients (MFCC) and Linear Frequency Cepstral Coefficients (LFCC).

9. The processor implemented method of claim 1, wherein the set of pre-defined performance metrics comprise accuracy, sensitivity, specificity and area under the receiver operating characteristic curve.

10. A system (100) comprising:
    one or more data storage devices (102) operatively coupled to one or more hardware processors (104) and configured to store instructions configured for execution by the one or more hardware processors to:
    receive a plurality of auscultation sound signals to be classified from a plurality of subjects;
    pre-process the received plurality of auscultation sound signals by resampling the plurality of auscultation sound signals and removing heart sound signals to obtain a plurality of lung sound signals, wherein the resampling is performed by down-sampling the plurality of auscultation sound signals to a pre-defined frequency based on a range of frequencies that provide optimum discrimination between healthy and abnormal lung sounds;

dividing the plurality of lung sound signals into a plurality of overlapping windows:

extract a set of features comprising two or more features types, wherein one of the features type is spectrogram features, and the other features type is selected from at least one of spectral features, wavelet features and cepstral features from the plurality of lung sound signals, wherein the extracted spectrogram features are median spectral powers (SP1 to SP58) across the plurality of overlapping windows, and wherein the median spectral powers are computed for a predefined number of equally spaced frequencies between 0.15 kHz-1.5 kHz of the plurality of lung sound signals, the pre-defined number of equally spaced frequencies being based on the computational complexity and frequency resolution;

select a plurality of features from the extracted set of features, wherein the selection of the plurality of discriminative features comprises ranking the extracted set of features in a decreasing order of importance and selecting a plurality of discriminative features based on an optimal number of features that result in a high performance value and a low standard deviation of a set of pre- defined performance metrics; and classify the plurality of lung sound signals based on the selected discriminative features.

11. The system of claim 10, wherein the extracted spectral features are areas under a normalized Power Spectral Density (PSD) estimate curve corresponding to a pre-defined number of frequency bands from 0-1.5 kHz ($PS_1$ to PS15), ratio of the spectral power below 500 Hz ($P_1$) to that from 500 Hz to 1500 Hz ($P_2$), spectral centroid ($S_{cent}$), spectral flux ($S_{flux}$), spectral rolloff ($S_{roll}$) and spectral kurtosis ($S_{kurt}$), wherein the pre-defined number of frequency bands is selected such that optimum discrimination between healthy and abnormal lung sounds is achieved.

12. The system of claim 10, wherein the extracted wavelet features ($W_1$ to $W_{21}$) are (i) median of absolute values of approximation and detail coefficients for decomposition levels obtained from the plurality of lung sound signals using a best mother wavelet and (ii) ratios thereof across sub-bands of a plurality of overlapping windows obtained by dividing the plurality of lung sound signals.

13. The system of claim 10, wherein the extracted cepstral features are mean ($mfccm_i$ and $lfccm_i$) and standard deviation ($mfccsd_i$ and $lfccsd_i$) of Mel Frequency Cepstral Coefficients (MFCC) and Linear Frequency Cepstral Coefficients (LFCC).

14. The system of claim 10, wherein the set of pre-defined performance metrics comprise accuracy, sensitivity, specificity and area under the receiver operating characteristic curve.

15. A computer program product comprising a non-transitory computer readable medium having a computer readable program embodied therein, wherein the computer readable program, when executed on a computing device, causes the computing device to:

receive a plurality of auscultation sound signals to be classified from a plurality of subjects;

pre-process the received plurality of auscultation sound signals by resampling the plurality of auscultation sound signals and removing heart sound signals to obtain a plurality of lung sound signals;

dividing the plurality of lung sound signals into a plurality of overlapping windows:

extract a set of features comprising two or more features types, wherein one of the features type is spectrogram features, and the other features type is selected from at least one of spectral features, wavelet features and cepstral features from the plurality of lung sound signals, wherein the extracted spectrogram features are median spectral powers (SP1 to SP58) across the plurality of overlapping windows, and wherein the median spectral powers are computed for a predefined number of equally spaced frequencies between 0.15 kHz-1.5 kHz of the plurality of lung sound signals, the pre-defined number of equally spaced frequencies being based on the computational complexity and frequency resolution;

select a plurality of features from the extracted set of features, wherein the selection of the plurality of discriminative features comprises ranking the extracted set of features in a decreasing order of importance and selecting a plurality of discriminative features based on an optimal number of features that result in a high performance value and a low standard deviation of a set of pre- defined performance metrics; and classify the plurality of lung sound signals based on the selected discriminative features.

* * * * *